(12) United States Patent
Lee et al.

(10) Patent No.: US 6,863,678 B2
(45) Date of Patent: Mar. 8, 2005

(54) CATHETER WITH A MULTILAYERED SHAFT SECTION HAVING A POLYIMIDE LAYER

(75) Inventors: Jeong S. Lee, Diamond Bar, CA (US); Edwin Wang, Tustin, CA (US); Roseminda J. White, Wildomar, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 152 days.

(21) Appl. No.: 09/957,526

(22) Filed: Sep. 19, 2001

(65) Prior Publication Data

US 2003/0055447 A1 Mar. 20, 2003

(51) Int. Cl.[7] .............................................. A61M 29/00
(52) U.S. Cl. .................. 606/192; 606/194; 604/103.09; 604/96.01
(58) Field of Search ............................... 606/192, 194; 604/103.09, 96.01

(56) References Cited

U.S. PATENT DOCUMENTS

| | | | |
|---|---|---|---|
| 4,563,181 A | * | 1/1986 | Wijayarathna et al. ...... 604/523 |
| 4,976,720 A | | 12/1990 | Machold et al. ............ 606/194 |
| 5,176,661 A | | 1/1993 | Evard et al. ................. 604/282 |
| 5,277,199 A | * | 1/1994 | DuBois et al. .............. 600/585 |
| 5,318,032 A | | 6/1994 | Lonsbury et al. ........... 128/658 |
| 5,318,526 A | * | 6/1994 | Cohen ....................... 604/95.04 |
| 5,364,357 A | * | 11/1994 | Aase ...................... 604/103.09 |
| 5,470,315 A | * | 11/1995 | Adams ................... 604/103.09 |
| 5,476,477 A | | 12/1995 | Burns |
| 5,538,513 A | | 7/1996 | Okajima |
| 5,545,134 A | * | 8/1996 | Hilaire et al. ........... 604/103.04 |
| 5,728,063 A | | 3/1998 | Preissman et al. ............. 604/96 |
| 5,759,173 A | | 6/1998 | Preissman et al. |
| 5,947,939 A | | 9/1999 | Mortier et al. ............... 604/280 |
| 6,024,722 A | | 2/2000 | Rau et al. ...................... 604/96 |
| 6,102,890 A | | 8/2000 | Stivland et al. ............... 604/96 |
| 6,165,166 A | * | 12/2000 | Samuelson et al. ......... 604/524 |
| 6,171,275 B1 | * | 1/2001 | Webster, Jr. .................. 604/20 |
| 6,217,565 B1 | * | 4/2001 | Cohen ........................ 604/525 |

FOREIGN PATENT DOCUMENTS

| | | |
|---|---|---|
| EP | 0 737 487 | 10/1996 |
| EP | 0 821 979 | 2/1998 |
| EP | 0 904 795 | 3/1999 |
| WO | WO 95/18647 | 7/1995 |
| WO | WO 96/03175 | 2/1996 |
| WO | WO 96/34646 | 11/1996 |

* cited by examiner

Primary Examiner—David O. Reip
Assistant Examiner—D. Jacob Davis
(74) Attorney, Agent, or Firm—Fulwider Patton Lee & Utecht LLP

(57) ABSTRACT

A catheter having an multilayered shaft section with a first layer formed of a polyimide first material and a second layer formed of a second material. In a presently preferred embodiment, the polyimide material is a thermoset polyimide. However, in alternative embodiments, a thermoplastic polyimide is used. The thermoset polyimide has a very high glass transition temperature (Tg) of approximately 400° C. (as measured by differential scanning calorimetry), and excellent dimensional stability at the processing temperature of polyamides commonly used in catheter components. As a result, during formation and assembly of the catheter, production of a thin polyimide layer with controlled dimensions is facilitated. The polyimide has a high modulus and provides a thin walled yet highly pushable shaft section, while the second layer provides kink resistance. In one embodiment, the second material is selected from the group consisting of a polyamide material and a polyurethane material.

23 Claims, 2 Drawing Sheets

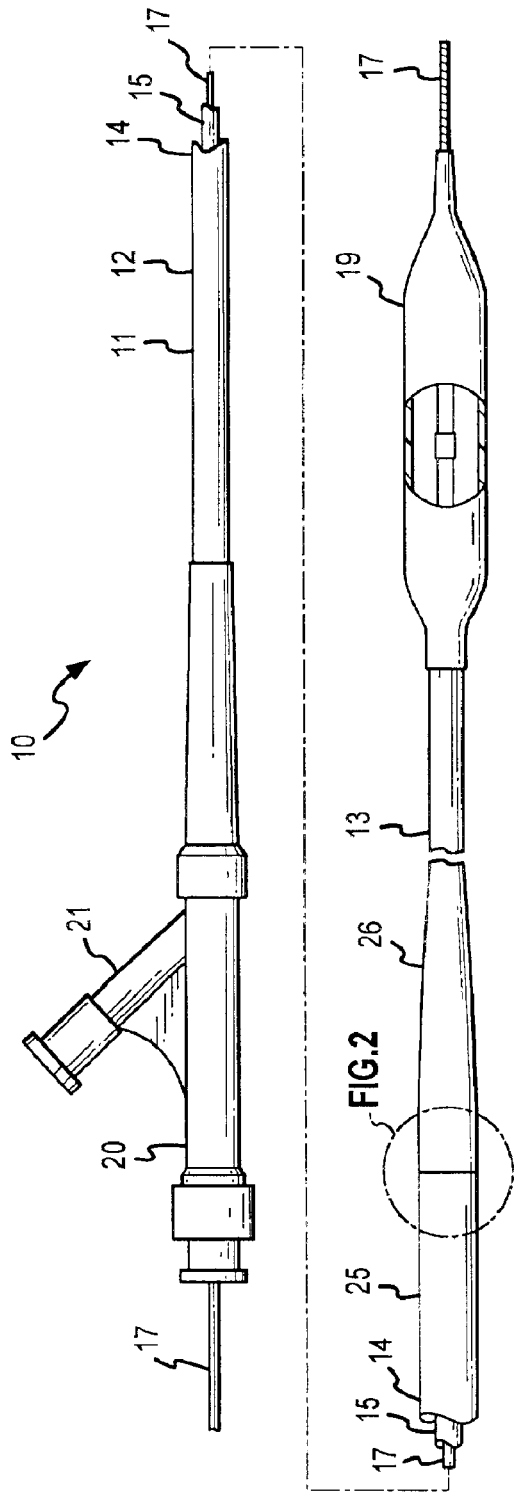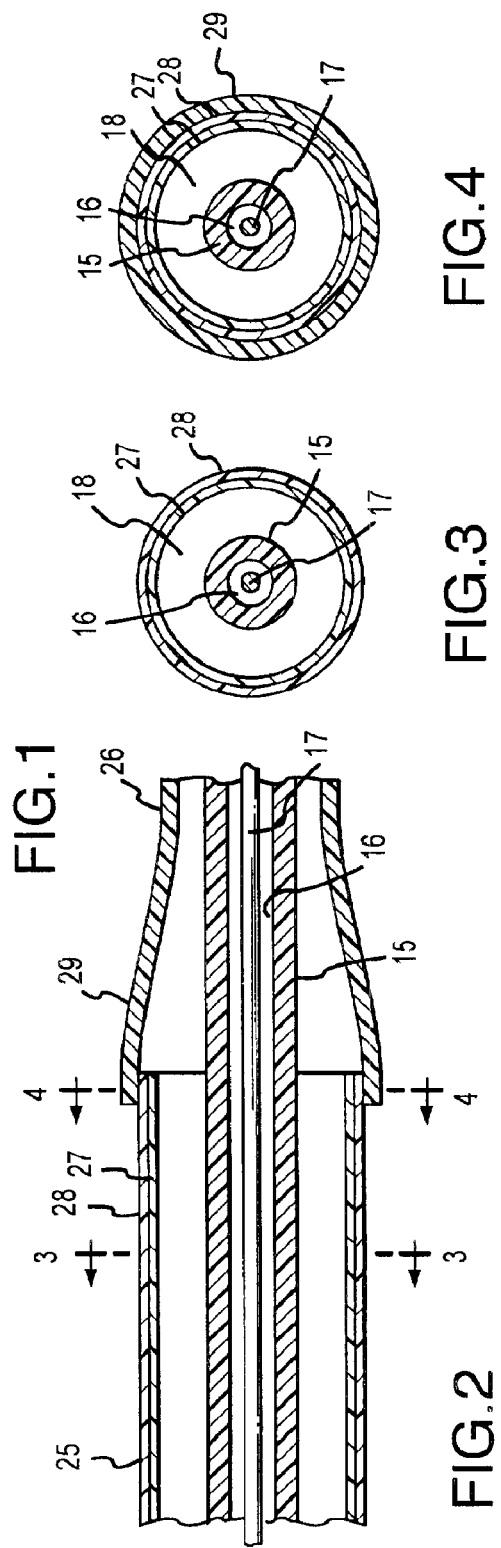

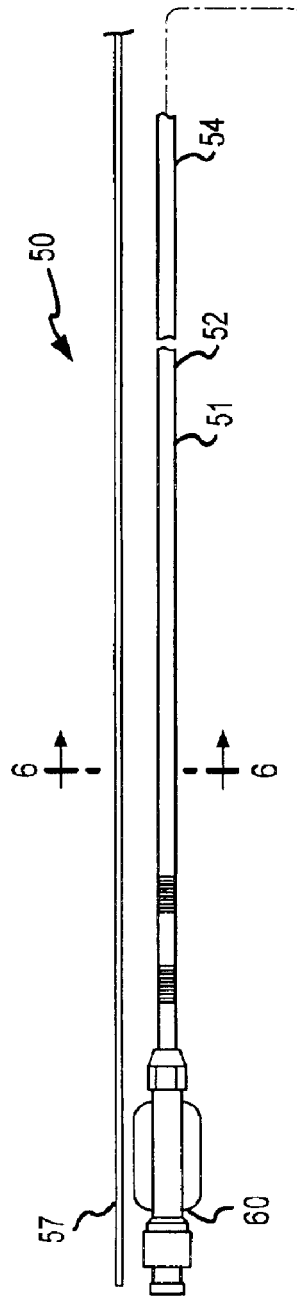
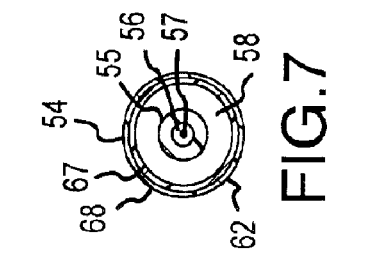
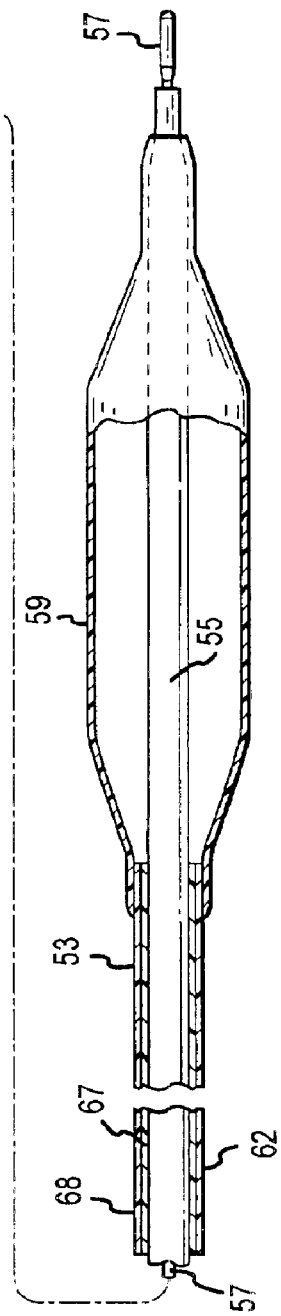
FIG. 5
FIG. 6
FIG. 7

CATHETER WITH A MULTILAYERED SHAFT SECTION HAVING A POLYIMIDE LAYER

BACKGROUND OF THE INVENTION

This invention generally relates to catheters, and particularly intravascular catheters for use in percutaneous transluminal coronary angioplasty (PTCA) or for the delivery of stents.

In a typical PTCA procedure, a dilatation balloon catheter is advanced over a guidewire to a desired location within the patient's coronary anatomy where the balloon of the dilatation catheter is positioned within the stenosis to be dilated. The balloon is then inflated with radiopaque liquid at relatively high pressures (generally 4–16 atmospheres) to dilate the stenosed region of the diseased artery. One or more inflations may be needed to effectively dilate the stenosis. Additionally, a stent may be implanted within the artery, typically by delivery to a desired location within the artery in a contracted condition on a balloon of a catheter which is similar in many respects to a balloon angioplasty catheter, and expansion to a larger diameter by inflation of the balloon.

An essential step in effectively performing a PTCA procedure is properly positioning the balloon catheter at a desired location within the coronary artery. To properly position the balloon at the stenosed region, the catheter must have good pushability and flexibility, to be readily advanceable within the tortuous anatomy of the patient's vasculature.

What has been needed is a catheter which is highly trackable within the patient's anatomy, with improved flexibility and pushability. The catheter of the present invention provides these and other advantages.

SUMMARY OF THE INVENTION

The invention is directed to a catheter having an multilayered shaft section with a first layer formed of a polyimide first material and a second layer formed of a second material. In a presently preferred embodiment, the polyimide material is a thermoset polyimide. However, in alternative embodiments, a thermoplastic polyimide is used. The thermoset polyimide has a very high glass transition temperature (Tg) of approximately 400° C. (as measured by differential scanning calorimetry), and excellent dimensional stability at the processing temperature of polyamides commonly used in catheter components. As a result, during formation and assembly of the catheter, production of a thin polyimide layer with controlled dimensions is facilitated. The polyimide has a high modulus and provides a thin walled yet highly pushable shaft section, while the second layer provides kink resistance.

In one embodiment, the second material is selected from the group consisting of a polyamide and a polyurethane. In one presently preferred embodiment, the second material is a polyamide, and the polyamide is selected from the group consisting of a nylon and a copolyamide such as polyether block amide (PEBAX). Although discussed below for convenience primarily in terms of a polyamide second layer, it should be understood that other materials such as a polyurethane may be used for the second layer in other embodiments. The polyimide first material is not compatible with the second material (e.g., polyamide or polyurethane), and consequently, the polyimide material is not fusion (i.e., thermal) bondable to the second material. The polyimide material is a high strength material preferably having a higher Shore durometer hardness than the polyamide layer. The high strength of the polyimide material allows the wall thickness of the polyimide first layer to be small for improved shaft flexibility and low profile. The polyamide layer provides a bonding layer which can be fusion bonded to polymeric materials compatible therewith and conventionally used for other catheter components, such as nylon, PEBAX, and polyurethane. Additionally, the polyamide layer contributes to the kink resistance of the catheter. In a presently preferred embodiment, the polyamide second layer is an outer layer forming an outer surface of the multilayered shaft section, and the polyimide first layer is an inner layer forming an inner surface of the multilayered shaft section.

In a presently preferred embodiment, the catheter is a balloon catheter generally comprising an elongated shaft having a proximal portion and a distal portion, with a balloon on the distal portion of the shaft. The balloon catheters of the invention may comprise a variety of suitable balloon catheters, including coronary and peripheral dilatation catheters, stent delivery catheters, drug delivery catheters, and the like.

The catheter shaft typically has an outer tubular member with a lumen therein which, in the case of a balloon catheter, is an inflation lumen in fluid communication with the balloon interior. The shaft also has an inner tubular member disposed at least in part within a portion of the outer tubular member lumen, with a lumen therein which is typically a guidewire receiving lumen. At least a section of the outer tubular member is the multilayered section in accordance with the invention. The multilayered shaft section of the invention may extend the full length of the outer tubular member, or alternatively, it may be a distal shaft section, a proximal shaft section, or a midshaft section bonded to an adjacent shaft section(s).

In one embodiment, the catheter is a rapid exchange type catheter, having a guidewire receiving lumen in a distal section of the catheter shaft. Rapid exchange catheters generally have a distal guidewire port in the distal end of the catheter, a proximal guidewire port spaced a relatively short distance proximally from the distal guidewire port and a relatively long distance from the proximal end of the catheter shaft, and a relatively short guidewire receiving lumen extending therebetween. In an alternative embodiment, the catheter is an over-the-wire type catheter having an elongated shaft with proximal and distal ends, a guidewire port in the proximal end, a guidewire port in the distal end, and a guidewire lumen extending therein from the distal end to the proximal end of the catheter shaft.

In a presently preferred embodiment, the polyamide second layer is in direct contact with the polyimide first layer around a circumference thereof. Thus, unlike catheter shafts having a braid layer between a first and second layer, the first layer and the second layer of the multilayered shaft section are not in whole or in part separated from one another by a braid, mesh or other layer.

In a presently preferred embodiment, the polyimide first layer is formed by a solution process, and not by melt extrusion. In a suitable solution forming process, a polyimide solution is dip, or otherwise, coated onto a neckable mandrel, as described in U.S. Pat. Nos. 4,826,706 and 4,659,622, and the Manufacturing Process section of the Phelps Dodge High Performance Conductors brochure, A Primer on Polyimide Tubing, pp. 1, incorporated herein by reference in their entireties, and then separated intact from the mandrel, to thereby produce a tubular member. The dip coated mandrel can be passed through dies to control the outer dimension of the polyimide layer, and the diameter of the removable mandrel determines the inner diameter of the polyimide tube. Similarly, the polyamide or polyurethane second layer is preferably applied as a solution onto the polyimide layer, in order to provide good contact and adhesion between the polyimide layer and the polyamide or polyurethane layer. Thus, although the polyimide material is not fusion bondable to the polyamide or polyurethane material, the solution coating process provides well adhered layers which remain together during component assembly and under the high inflation pressures used during inflation of the catheter balloon. As a result, a separate adhesive or compatibilizing layer is not required between the polyimide first layer and the second layer, and, consequently, the multilayered shaft section of the invention has excellent flexibility, manufacturability, and low profile.

The catheter of the invention is highly pushable, flexible, and kink resistant due to the synergy of the materials used in the multilayered shaft section. The polyimide material has a high modulus which allows for a very thin walled yet high strength shaft. The high flexural modulus of the polyimide layer provides excellent push transmission along the shaft length during advancement within the patient's vasculature and across a lesion. Moreover, the high modulus polyimide layer provides the ability to be inflated to high inflation pressure without rupturing during balloon inflation. The thin walled shaft section provides a low profile shaft without sacrificing lumen size. Additionally, the polyamide layer provides an outer layer which is readily fusion bondable with polymeric materials commonly used in other catheter components such as balloons or shaft sections. Thus, the flexible and pushable distal shaft section provides a catheter with excellent trackability, and allows easy advancement over a guidewire and maneuvering within the patient's tortuous anatomy, to position the operative portion of the catheter at a desired location within the patient. These and other advantages of the invention will become more apparent from the following detailed description of the invention and the accompanying exemplary drawings.

BRIEF DESCRIPTION OF THE DRAWINGS

FIG. 1 is an elevational view of a catheter which embodies features of the invention.

FIG. 2 is an enlarged view, partially in section, of the portion of the catheter shown in FIG. 1, taken within circle 2.

FIG. 3 is a transverse cross sectional view of the catheter shown in FIG. 2, taken along line 3—3.

FIG. 4 is a transverse cross sectional view of the catheter shown in FIG. 2, taken along line 4—4.

FIG. 5 is an elevational view of an alternative embodiment of a catheter which embodies features of the invention, having a rapid exchange distal guidewire lumen.

FIG. 6 is a transverse cross sectional view of the catheter shown in FIG. 5, taken along line 6—6.

FIG. 7 is a transverse cross sectional view of the catheter shown in FIG. 5, taken along line 7—7.

DETAILED DESCRIPTION OF THE INVENTION

FIGS. 1–4 illustrate an over-the-wire type balloon catheter 10 embodying features of the invention. Catheter 10 generally comprises an elongated catheter shaft 11 having a proximal end, a distal end, a proximal shaft section 12, a distal shaft section 13, an outer tubular member 14, and an inner tubular member 15. Inner tubular member 15 defines a guidewire lumen 16 adapted to slidingly receive a guidewire 17, and the coaxial relationship between outer tubular member 14 and inner tubular member 15 defines annular inflation lumen 18 (see FIGS. 3 and 4, illustrating transverse cross sections of the catheter 10 of FIG. 1, taken along lines 3—3 and 4—4, respectively). An inflatable balloon 19 is disposed on the distal shaft section 13, having a proximal skirt section sealingly secured to the distal end of outer tubular member 14, and a distal skirt section sealingly secured to the distal end of inner tubular member 15, so that its interior is in fluid communication with inflation lumen 18. An adapter 20 at the proximal end of the shaft is configured to provide access to guidewire lumen 17, and to direct inflation fluid through arm 21 into inflation lumen 18. Balloon 19 has an inflatable working length located between tapered sections of the balloon. FIG. 1 illustrates the balloon 19 in an uninflated configuration prior to inflation. The distal end of catheter may be advanced to a desired region of a patient's body lumen in a conventional manner, and balloon 19 inflated to perform a procedure such as dilatation of a stenosis.

In the embodiment illustrated in FIGS. 1–4, the outer tubular member has a proximal section 25, and a distal section 26. As best illustrated in FIG. 2, showing an enlarged longitudinal cross sectional view of the section of the catheter 10 shown in FIG. 1, taken within circle 2, the proximal section 25 is multilayered with a first layer 27 of a polyimide material and a second layer 28 of a material which is different from the first material, and which is preferably a polyamide material or a polyurethane. A presently preferred polyimide for the first layer is available from Phelps Dodge High Performance Conductors. Preferably, the polyimide is a thermoset polyimide with excellent dimensional stability, which thus has a cross linked 3-dimensional network maintained a high temperatures. A presently preferred polyamide for the second layer is PEBAX, available from Elf Autochem. A presently preferred polyurethane for the second layer is polyurethane N, available from Phelps Dodge High Performance Conductors. The second layer 28 is on an outer surface of the first layer 27. As illustrated in the figures, the second layer 28 is a solid-walled layer, which is in direct contact with the first layer 27 around a circumference of the first layer 27. Thus, the second layer 28 is not separated from the first layer 27 by an intermediate layer or braid, and is not itself a braid or mesh.

In the embodiment of FIGS. 1–4, the second layer 28 of the proximal section 25 forms an outer surface of the multilayered section of the outer tubular member 14. Thus, although a coating such as a lubricious coating conventionally used on catheter shafts may optionally be provided on at least a section of an outer surface of the multilayered shaft section, a structural or reinforcing layer is not on an outer surface of the second layer 28 in the embodiment of FIG. 1. The first layer 27 forms an inner surface of the multilayered section of the outer tubular member 14. An optional lubricious inner liner such as a PTFE or HDPE layer may be provided on an inner surface of the first layer 27, as conventionally known for catheter shafts.

In the embodiment illustrated in FIG. 1, the distal section 26 of the outer tubular member 14 comprises a single layered tubular member 29, with a proximal end bonded to a distal end of the proximal section 25 of the outer tubular member 14. In a presently preferred embodiment, the distal section 26 is formed of a polymeric material, such as polyether block amide (PEBAX), which is compatible with a polyamide material such as PEBAX and nylon, forming the second layer 28 of the proximal section 25, to allow for fusion bonding the two sections together. However, a variety of suitable methods of bonding can be used including adhesive bonding. Additionally, although a lap joint is illustrated in FIG. 2 between the proximal and distal sections 25/26, a variety of suitable joints may be used including a butt joint, or a lap joint in which the outer diameter of the proximal section 25 is reduced at the joint so that the distal section 26 is flush with the proximal section.

In an alternative embodiment (not shown), the multilayered section of the outer tubular member 14 is the distal section 26, and the balloon proximal skirt section is fusion bonded to the second layer 28 of the outer tubular member 14 multilayered distal section.

FIGS. 5–7 illustrate an alternative embodiment of the invention, in which the balloon catheter 50 is a rapid exchange catheter with an outer tubular member 54 having a multilayered distal section 56. A illustrated in FIG. 5, catheter 50 generally comprises an elongated catheter shaft 51 having a proximal end, a distal end, a proximal shaft section 52, a distal shaft section 53, an outer tubular member 54, and an inner tubular member 55. Inner tubular member 55 defines a guidewire lumen 56 adapted to slidingly receive a guidewire 57. Inflation lumen 58 is defined by the outer tubular member 54. An inflatable balloon 59 is disposed on the distal shaft section 53, having a proximal skirt section sealingly secured to the distal end of outer tubular member 54, and a distal skirt section sealingly secured to the distal end of inner tubular member 55, so that its interior is in fluid communication with inflation lumen 58. An adapter 60 at the proximal end of the shaft is configured to direct inflation fluid into inflation lumen 58.

In the embodiment illustrated in FIG. 5, the outer tubular member 54 comprises a proximal section 61, a distal section 62, and a midshaft section 63 having a proximal end bonded to the proximal section 61 and a distal end bonded to the distal section 62. A guidewire proximal port 64 in a side wall of the midshaft section 63 is in fluid communication with the lumen 56 of the inner tubular member 55, and with a distal guidewire port in the distal end of the shaft. As shown in FIG. 5, the guidewire 57 exits the catheter proximally from the guidewire proximal port 64 and extends alongside and exteriorly of the proximal section 61 to the proximal end of the catheter 50. Although the guidewire proximal port 64 is in the midshaft section, in an alternative embodiment (not shown) it is located in the proximal section 61 or the distal section 63. Additionally, in an alternative embodiment of rapid exchange catheter 50, the outer tubular member 54 comprises the proximal section 61 directly bonded to the distal section 62, without a midshaft section therebetween (not shown). A support mandrel 65 is disposed in the inflation lumen 58, with a distal end distal to the guidewire proximal port 64. The mandrel is typically a metal member, such as a stainless steel or NiTi member, enhancing the pushability of the catheter 50.

In the embodiment illustrated in FIG. 5, the distal section 62 of the outer tubular member 54 is a multilayered section with a first layer 67 of a polyimide material and a second layer 68 of a material which is different from the first material, and which is preferably a polyamide material. The multilayered distal section 62 is similar to the multilayered section of the catheter 10 discussed above in relation to the embodiment of FIGS. 1–4, and the discussion above relating to the first layer 27 and second layer 28 of the multilayered proximal section 25 of catheter 10 applies as well to first and second layers 67/68 of the multilayered distal section 62 of catheter 50. In a presently preferred embodiment, the second layer 68 of the multilayered distal section 62 of the outer tubular member 54 is a polyether block amide (PEBAX) material on the polyimide first layer 61, providing a highly kink resistant and pushable rapid exchange catheter. Balloon 59 has a proximal skirt section bonded to the second layer 68 of the distal section 62 of outer tubular member 54.

When the catheter of the invention is used in an angioplasty procedure, the balloon catheter of the invention is advanced over the guidewire until the balloon is properly positioned across the stenosis. The balloon can be inflated in a conventional manner by introducing inflation fluid through the inflation lumen. After one or more inflations, the balloon is deflated and the catheter removed from the patient. A similar procedure is used when the balloon has a stent (not shown) mounted thereon for implanting the stent in the body lumen.

The length of the dilatation catheter is generally about 137 to about 145 centimeters, and typically about 140 centimeters for PTCA. The outer tubular member 14/54 distal section has an outer diameter (OD) of about 0.028 to about 0.036 inch (0.70–0.91 mm), and an inner diameter (ID) of about 0.024 to about 0.035 inch (0.60–0.89 mm), and the outer tubular member 14/54 proximal section has an OD of about 0.017 to about 0.034 inch (0.43–0.87 mm), and an inner diameter (ID) of about 0.012 to about 0.022 inch (0.30–0.56 mm). The inner tubular member 15/55 has an OD of about 0.017 to about 0.026 inch (0.43–0.66 mm), and an ID of about 0.015 to about 0.018 inch (0.38–0.46 mm) depending on the diameter of the guidewire to be used with the catheter. In one embodiment, the polyimide layer is about 0.0005 inches (0.0127 mm) to about 0.0015 inches (0.038 mm) thick, and preferably about 0.0005 inches (0.0127 mm) to about 0.00075 inches (0.019 mm) thick, and the second layer (e.g., of polyamide or polyurethane) is about 0.00075 inch (0.019 mm) to about 0.00125 inches (0.03 mm) thick, preferably about 0.001 (0.025 mm) to about 0.00125 inches (0.03 mm) thick. In a presently preferred embodiment, the polyimide first layer has a smaller thickness than the second layer.

While the present invention has been described herein in terms of certain preferred embodiments, those skilled in the art will recognize that modifications and improvements may be made without departing form the scope of the invention. For example, while the catheter illustrated in the figures has coaxial inner and outer tubular members, other conventional catheter shaft configurations can be used along at least a section of the catheter, such as side-by-side, dual lumen configurations. Moreover, while individual features of one embodiment of the invention may be discussed or shown in the drawings of the one embodiment and not in other embodiments, it should be apparent that individual features of one embodiment may be combined with one or more features of another embodiment or features from a plurality of embodiments

What is claimed is:

1. A catheter, comprising an outer tubular member defining a lumen, and an inner tubular member disposed at least in part within the outer tubular member lumen and defining a lumen, the outer tubular member having at least a section thereof which is multilayered with a first layer of a polyimide first material, and a second layer of a second material having a lower Shore durometer hardness than the polyamide material and selected from the group consisting of a polyamide material and a polyurethane material, the second layer is not in whole or in part separated from the first layer by a braid or mesh reinforcement, and the second layer is in direct contact with a surface of the first layer around a circumference of the first layer, and wherein the polyimide material is not fusion bondable to the polyamide or polyurethane material.

2. The catheter of claim 1 wherein the polyimide material is selected from the group consisting of a themoplastic polyimide and a thermoset polyimide.

3. The catheter of claim 1 wherein the polyimide is a thermoset polyimide.

4. A balloon catheter, comprising;
   a) an elongated shaft having a proximal end, a distal end, an outer tubular member with a lumen therein, and an inner tubular member with a lumen therein disposed within at least a portion of the outer tubular member lumen, the outer tubular member having at least a section thereof which is multilayered with a first layer of a polyimide first material, and a second layer of a second material selected from the group consisting of a polyamide material and a polyurethane material, the second layer being a solid-walled layer without a braid or mesh reinforcement, and wherein the polyimide material is not fusion bondable to the polyamide or polyurethane material; and
   b) a balloon on a distal portion of the shaft, having an interior in fluid communication with the outer tubular member lumen.

5. The balloon catheter of claim 4 wherein the polyimide material is selected from the group consisting of a thermoplastic polyimide and a thermoset polyimide.

6. The balloon catheter of claim 4 wherein the polyimide material is a thermoset polyimide.

7. The balloon catheter of claim 4 wherein the polyamide material is selected from the group consisting of nylon and polyether block amide.

8. The balloon catheter of claim 4 wherein the polyimide material has a higher Shore durometer hardness than the polyamide or polyurethane material.

9. The balloon catheter of claim 8 wherein the second layer is on an outer surface of the first layer.

10. The balloon catheter of claim 4 wherein the second layer forms an outer surface of the multilayered section of the outer tubular member.

11. The balloon catheter of claim 4 wherein the first layer forms an inner surface of the multilayered section of the outer tubular member.

12. The balloon catheter of claim 4 wherein the second layer is in direct contact with the outer surface of the first layer around a circumference of the first layer.

13. The balloon catheter of claim 4 wherein the mulitlayered section of the outer tubular member is a distal section of the outer tubular member, having a proximal end bonded to a proximal section of the outer tubular member.

14. The balloon catheter of claim 13 wherein the balloon has a proximal skirt section fusion bonded to the second layer of the outer tubular member multilayered distal section.

15. The balloon catheter of claim 4 wherein the multilayered section of the outer tubular member is a proximal section of the outer tubular member, having a distal end bonded to a distal section of the outer tubular member.

16. The balloon catheter of claim 4 wherein the inner tubular member extends from the distal end of the shaft to the proximal end of the shaft.

17. The balloon catheter of claim 4 the inner tubular member extends from the distal end of the shaft to a location spaced distally of the proximal end of the shaft.

18. The balloon catheter of claim 17 wherein the outer tubular member comprises a proximal section, a distal section, and a midshaft section having a proximal end bonded to the proximal section of the outer tubular member and a distal end bonded to the distal section of the outer tubular member, and having a guidewire proximal port in a side wall of the midshaft section which is in fluid communication with the lumen of the inner tubular member, and the multilayered section of the outer tubular member is the distal section thereof.

19. The balloon catheter of claim 4 wherein a separate adhesive or compatibilizing layer is not between the first layer and the second layer, so that the first and second layers are in direct contact and adhered together.

20. A balloon catheter, comprising;
   a) an elongated shaft having a proximal end, a distal end, an outer tubular member with an inflation lumen therein, and an inner tubular member with a guidewire lumen therein disposed within at least a portion of the inflation lumen, the outer tubular member having at least a section thereof which is multilayered with a first layer of a thermoset polyimide first material forming an inner surface of the multilayered section of the outer tubular member, and a second layer of a second material different from the thermoset polyimide material and having a lower Shore durometer hardness than the polyimide material, and the second layer is not in whole or in part separated from the first layer by a braid or mesh reinforcement, and is on an outer surface of the first layer and forms an outer surface of the multilayered section of the outer tubular member, and wherein the polyimide material is not fusion bondable to the second material; and
   b) a balloon on a distal portion of the shaft, having an interior in fluid communication with the inflation lumen.

21. The balloon catheter of claim 20 wherein the second layer is in direct contact with the outer surface of the first layer around a circumference of the first layer.

22. The balloon catheter of claim 20 wherein the second material is selected from the group consisting of a polyamide material and a polyurethane material.

23. The balloon catheter of claim 20 wherein the balloon has a proximal skirt section fusion bonded to the second layer of the multilayered outer tubular member section.

* * * * *

UNITED STATES PATENT AND TRADEMARK OFFICE
CERTIFICATE OF CORRECTION

PATENT NO. : 6,863,678 B2
DATED : March 8, 2005
INVENTOR(S) : Jeong S. Lee et al.

It is certified that error appears in the above-identified patent and that said Letters Patent is hereby corrected as shown below:

Column 5,
Line 20, delete "A illustrated" and insert -- As illustrated --.

Column 6,
Line 45, delete "form" and insert -- from --.
Line 64, delete "polya" and insert -- polyi --.

Column 7,
Line 7, delete "themoplastic" and insert -- thermoplastic --.

Signed and Sealed this

Sixth Day of June, 2006

JON W. DUDAS
*Director of the United States Patent and Trademark Office*